US007522960B2

(12) United States Patent
Seligman et al.

(10) Patent No.: US 7,522,960 B2

(45) Date of Patent: Apr. 21, 2009

(54) VARIABLE SENSITIVITY CONTROL FOR A COCHLEAR IMPLANT

(75) Inventors: Peter Misha Seligman, Victoria (AU); Hugh McDermott, Victoria (AU)

(73) Assignee: Cochlear Limited, Lane Cove, New South Wales (AU)

( * ) Notice: Subject to any disclaimer, the term of this patent is extended or adjusted under 35 U.S.C. 154(b) by 519 days.

(21) Appl. No.: 10/474,631

(22) PCT Filed: Apr. 11, 2002

(86) PCT No.: PCT/AU02/00463

§ 371 (c)(1), (2), (4) Date: Apr. 21, 2004

(87) PCT Pub. No.: WO02/084866

PCT Pub. Date: Oct. 24, 2002

(65) Prior Publication Data

US 2004/0172242 A1 Sep. 2, 2004

(30) Foreign Application Priority Data

Apr. 11, 2001 (AU) .................................... PR4386

(51) Int. Cl.
*A61N 1/00* (2006.01)

(52) U.S. Cl. ........................................................ 607/55

(58) Field of Classification Search ............. 607/55-57; 381/57, 71.1, 94.1

See application file for complete search history.

(56) References Cited

U.S. PATENT DOCUMENTS 4,532,930 A 8/1985 Crosby et al.
5,907,622 A 5/1999 Dougherty

FOREIGN PATENT DOCUMENTS

| | | | |
|---|---|---|---|
| EP | 0 875 989 | A2 | 11/1998 |
| GB | 2 289 583 | | 11/1995 |
| GB | 2 292 275 | | 2/1996 |
| WO | WO94/07305 | | 3/1994 |
| WO | WO96/13096 | | 5/1996 |
| WO | WO98/58448 | | 12/1998 |

*Primary Examiner*—Mark W Bockelman
(74) *Attorney, Agent, or Firm*—Christie, Parker & Hale, LLP

(57) ABSTRACT

The invention provides an amplifier for providing adaptive operation of an auditory prosthesis. The amplifier receives an input signal and produces an output signal, and comprises a gain control. Estimates of the current noise floor value of the input signal are obtained, and in response to a change in the current estimated noise floor value, the gain control alters the amount of gain applied to the input signal. Further, in response to the change in the current estimated noise floor value, the gain control alters a gain compression ratio of the amplifier across the dynamic range of the amplifier. The present invention allows for adaptive operation of the amplifier responsive to varying noise floor levels, while maintaining desired gain characteristics of the amplifier across a range of input signal levels.

149 Claims, 6 Drawing Sheets

61
Read ADC to get output level
62
Convert to dB
63
Subtract GAIN to get input LEVEL
64
Is input level below lowest level Emin?
Y
N
65
Update lowest level Emin
66
Raise Emin slightly
67
Calculate adaptive AGC threshold Tx
68
If Tx>Tinf then Tx = Tinf
69
Is LEVEL above AGC threshold Tx?
Y
N
70
Lower GAIN by amount above AGC threshold
71
Raise GAIN slightly

VARIABLE SENSITIVITY CONTROL FOR A COCHLEAR IMPLANT

CROSS-REFERENCE TO RELATED APPLICATION

This application is a National Phase Patent Application of International Application Number PCT/AU02/00463, filed on 11 Apr. 2002, which claims priority of Australian Patent Application No. PR 4386, filed 11 Apr. 2001.

TECHNICAL FIELD

The present invention relates to a method and device for controlling the sensitivity and gain of an amplifier used in a hearing device, such as a hearing aid or cochlear implant.

BACKGROUND ART

In many people who are profoundly deaf, the reason for deafness is absence of, or destruction of, the hair cells in the cochlea which transduce acoustic signals into nerve impulses. These people are thus unable to derive suitable benefit from conventional hearing aid systems, no matter how loud the acoustic stimulus is made, because there is damage to or absence of the mechanism for nerve impulses to be generated from sound in the normal manner.

It is for this purpose that cochlear implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve. U.S. Pat. No. 4,532,930, the contents of which are incorporated herein by reference, provides a description of one type of traditional cochlear implant system.

Typically, cochlear implant systems have consisted of essentially two components, an external component commonly referred to as a processor unit and an internal implanted component commonly referred to as a stimulator/receiver unit. Traditionally, both of these components have cooperated together to provide the sound sensation to a user.

The external component has traditionally consisted of a microphone for detecting sounds, such as speech and environmental sounds, a speech processor that converts the detected sounds, particularly speech, into a coded signal, a power source such as a battery, and an external transmitter coil.

The coded signal output by the speech processor is transmitted transcutaneously to the implanted stimulator/receiver unit situated within a recess of the temporal bone of the user. This transcutaneous transmission occurs via the external transmitter coil which is positioned to communicate with an implanted receiver coil provided with the stimulator/receiver unit. This communication serves two essential purposes, firstly to transcutaneously transmit the coded sound signal and secondly to provide power to the implanted stimulator/receiver unit. Conventionally, this link has been in the form of an RF link, but other such links have been proposed and implemented with varying degrees of success.

The implanted stimulator/receiver unit traditionally includes a receiver coil that receives the coded signal and power from the external processor component, and a stimulator that processes the coded signal and outputs a stimulation signal to an intracochlea electrode assembly which applies the electrical stimulation directly to the auditory nerve producing a hearing sensation corresponding to the original detected sound.

Traditionally, the external componentry has been carried on the body of the user, such as in a pocket of the user's clothing, a belt pouch or in a harness, while the microphone has been mounted on a clip mounted behind the ear or on the lapel of the user.

More recently, due in the main to improvements in technology, the physical dimensions of the speech processor have been able to be reduced allowing for the external componentry to be housed in a small unit capable of being worn behind the ear of the user. This unit allows the microphone, power unit and the speech processor to be housed in a single unit capable of being discretely worn behind the ear, with the external transmitter coil still positioned on the side of the user's head to allow for the transmission of the coded sound signal from the speech processor and power to the implanted stimulator unit.

In earlier versions of speech processors, the processor used feature extraction strategies to identify the speech features present in the signal from the microphone and encode them as patterns of electrical stimulation. Typically, the features of the speech that were extracted were the fundamental frequency (or voice pitch) and the amplitudes and frequencies of the first and second formants of the speech spectrum. Such processing had the advantage that the hardware required to perform the feature extraction could be relatively simple so leading to a relatively low power consumption. Strategies that employed this feature extraction philosophy were found to work particularly well when the user was listening to a single voice in a quiet environment, however, when the user was in an environment with background noise the strategy was not nearly as successful. If, for example, two people were speaking at the same time, then two first formants would be mixed. The processor in expecting only one formant provided a single estimate of this formant which was a mixture of the two. The result was a signal which the user could not readily understand.

A new approach was subsequently developed that provided a full range of spectral information without any attempt by the hardware to fit it into a preconceived mould. The user was then given an opportunity to listen for the particular information of interest and identify the speech features themselves, in the presence of the background noise. In this approach, the overall sound spectrum is analysed and divided into a number of frequency bands with the electrodes stimulated in a tonotopic fashion according to the energy in those bands. This has a number of advantages as it saves power, allows a higher stimulation rate to be employed since time is not wasted in presenting unimportant stimuli, and also serves to decrease the annoyance of background noise.

Although there are differences between speech processors for different cochlear implants and also speech processors used in hearing aid applications, there are also many common features. A speech processor firstly typically includes a preamplifier and automatic gain control (AGC). The preamplifier amplifies the very low signal detected from the microphone to a suitable level that can be handled by the rest of the speech processor. The AGC controls the level of the signal so that it does not overload or distort. The AGC can have what is known as infinite compression in that the signal is amplified by a fixed gain until the output signal reaches a certain maximum level, at which the gain is reduced to prevent the output signal from exceeding that level. For example, the gain may be controlled in order to ensure that an output signal never exceeds a maximum comfort value for the user.

It has been found that users of cochlear implant systems that have an automatic gain control (AGC) tend to set the sensitivity to a level such that the AGC does not enter infinite compression except at high input signal levels, such as when they themselves speak. The motive for this is that setting the sensitivity higher means that the gain is reduced during speech that the user wants to hear, but is increased when the speaker stops, thus amplifying the background noise. Setting the sensitivity lower results in some of the signal falling outside the stimulation range, and so reducing speech perception. In summary, patients set the sensitivity control to maximise the perceived signal to noise ratio, ie. the ratio between speech and background noise in the absence of speech. In general, the sensitivity control is set so that the background noise is not too obtrusive.

A problem can occur with this system when a user is faced with an environment where the level of background noise is varying. To address this problem, an Automatic Sensitivity Control (ASC) has been devised. The ASC controls the background noise level by constantly monitoring the signal from the microphone and recording the minimum level to which it drops over a period of several seconds (generally 5-10 seconds). This minimum level is called the noise floor. The ASC adjusts the gain so that the noise floor is held below a predetermined breakpoint, usually so that the user's threshold hearing level corresponds approximately to the noise floor. The gain sensitivity adjustment may be made manually or by an automatic means such as is described in International Publication No WO 96/13096, the contents of which are incorporated by reference. Although this system provides improved listening comfort for the user, the system does have the disadvantage that at low speech levels, a step of simply linearly increasing the amount of gain is insufficient to maintain such speech perception at a satisfactory level.

The present inventors have recognised the shortcomings of current hearing device sensitivity control techniques and practices in the prior art and accordingly have sought to provide an improved system and method of controlling the sensitivity of hearing devices, such as cochlear implants.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY OF THE INVENTION

According to a first aspect, the present invention resides in an amplifier for providing adaptive operation of an auditory prosthesis, the amplifier operable to receive an input signal and produce an output signal, the amplifier comprising:

a gain control means; and means to provide a current estimated noise floor value of the input signal, wherein, in response to a change in the current estimated noise floor value, the gain control means is operable to alter the amount of gain applied to the input signal.

According to a second aspect, the present invention resides in an amplifier for providing adaptive operation of an auditory prosthesis, the amplifier operable to receive an input signal and produce an output signal, the amplifier comprising:

a gain control means; and means to provide a current estimated noise floor value of the input signal, wherein, in response to a change in the current estimated noise floor value, the gain control means is operable to alter the amount of gain applied to the input signal, and wherein, in response to a change in the current estimated noise floor value, the gain control means is operable to alter a gain compression ratio of the amplifier across at least a portion of the dynamic range of the amplifier.

According to a third aspect, the present invention resides in an amplifier for providing adaptive operation of an auditory prosthesis, the amplifier operable to receive an input signal and produce an output signal, the amplifier comprising a gain control means, wherein the gain control means is operable to control the gain of the amplifier in response to a current estimated noise floor value such that the amplifier will only produce an output signal which is greater than or substantially equal to a hearing threshold value when the input signal of the amplifier is greater than or substantially equal to the current estimated noise floor value, and wherein the gain control means is operable to alter the dynamic range of the amplifier in response to a change in the current estimated noise floor value.

Embodiments of the invention may thus ensure that all input signals which are substantially equal to or above the current estimated noise floor value will be converted to an output signal above or at the hearing threshold value, and accordingly, will be passed to the auditory nerve of a user of an auditory prosthesis incorporating such an amplifier in a perceptible manner. Further, by altering the gain of the amplifier in response to a change in the current estimated noise floor value, or by altering the gain compression ratio, or by altering the dynamic range of the amplifier in response to a change in the current estimated noise floor value, the present invention allows for adaptive operation of the amplifier responsive to varying noise floor levels, while maintaining desired gain characteristics of the amplifier across a range of input signal levels.

According to a fourth aspect, the present invention resides in a speech processing means for an auditory prosthesis, the speech processing means comprising:

an amplifying means which is operable to receive an input signal provided by a microphone of the auditory prosthesis, and which is operable to produce an output signal; and a gain control means operable to control the gain of the amplifier in response to a current estimated noise floor value such that the amplifier will only produce an output signal which is greater than or substantially equal to a hearing threshold value when the input signal of the amplifier is greater than or substantially equal to the current estimated noise floor value, and wherein the gain control means is operable to alter the dynamic range of the amplifier in response to a change in the current estimated noise floor value.

According to a fifth aspect, the present invention resides in a method for controlling the gain of an amplifying means of an auditory prosthesis, the amplifying means operable to receive an input signal and produce an output signal, the method comprising the steps of:

determining a current estimated noise floor value; and in response to a change in the current estimated noise floor value, altering the gain applied to the input signal by the amplifying means.

According to a sixth aspect, the present invention resides in a method for controlling the gain of an amplifying means of an auditory prosthesis, the amplifying means operable to receive an input signal and produce an output signal, the method comprising the steps of:

determining a current estimated noise floor value;

in response to a change in the current estimated noise floor value, altering the gain applied to the input signal by the amplifying means; and in response to the change in the current estimated noise floor value, altering a gain compression ratio across at least a portion of the dynamic range of the amplifying means.

According to a seventh aspect, the present invention resides in a method for controlling the gain of an amplifying means of an auditory prosthesis, the amplifying means operable to receive an input signal and produce an output signal, the method comprising the steps of:

determining a current estimated noise floor value;

controlling the gain of the amplifier in response to the current estimated noise floor value such that the amplifier only produces an output signal which is greater than or substantially equal to a hearing threshold value when the input signal of the amplifier is greater than or substantially equal to the current estimated noise floor value; and altering the dynamic range of the amplifier in response to a change in the current estimated noise floor value.

The current estimated noise floor value is preferably derived from the input signal, and may be substantially continuously updated or only periodically updated. Ongoing derivation and updating of the current estimated noise floor value enables the amplifier to adapt to ongoing changes in the current estimated noise floor value. In particular, in implementing the method of the fifth to seventh aspects of the present invention, it will be appreciated that the step of determining a current estimated noise floor value may for example be carried out continuously, periodically or repeatedly, and may be carried out simultaneously with one or more other steps of the method of the present invention. For instance, the step of determining a current estimated noise floor value may comprise continuously monitoring an envelope of an input signal and determining the current estimated noise floor value based on detected minima of that envelope.

Typically, the amplifier gain may vary for differing input signal levels. That is, the amplifier response may be non-linear for changing input signal levels.

It will be appreciated that alteration of the amplifier response in the dynamic range responsive to a varying noise floor level may be implemented in many different ways, for example to allow testing or to adapt to individual users' requirements. In preferred embodiments of the above aspects of the invention, the dynamic range of the amplifier is increased in response to a decrease in the current estimated noise floor value. In such embodiments, the dynamic range of the amplifier is preferably decreased in response to an increase in the current estimated noise floor value.

Preferably, the amplifier response is continuous, monotonic and increasing for all output signal levels between the hearing threshold value and the maximum comfort value. The amplifier preferably produces an output signal equal in magnitude to the hearing threshold value when the input signal equals the current estimated noise floor level. Preferably, the gain control means ensures that the amplifier does not produce any output signals which exceed a maximum comfort level, even when the input signal is at high levels. For example, the amplifier may produce a constant output signal level for all input signal levels above a maximum input level. That is, the amplifier may be controlled to enter infinite compression when the input signal goes beyond the maximum input level. The maximum input level could, for example, be in the range 60-90 dB, and could be around 70 dB. The setting of a maximum output level from the amplifying means serves to ensure that no damage is caused to the auditory prosthesis, such as the electrode array of a cochlear implant, and/or avoids discomfort to the user.

The amplifier may be controlled to have a substantially zero gain for input signals below the current estimated noise floor value, such that substantially no output signal is produced when input signals at such levels are received by the amplifier. Alternatively, the gain of the amplifier may be kept constant for such input signals, for example to allow summation of input signals below the hearing threshold, which can in fact produce an audible stimulus.

It is to be understood that the amplifier may have a gain which is greater than one, equal to one, or less than one in magnitude. The gain may be negative.

In one embodiment, the auditory prosthesis can be a hearing aid or a cochlear implant.

In a preferred embodiment, the amplifying means provides linear gain of input signals which are greater in amplitude than the current estimated noise floor value, and are lesser in amplitude than the input signal level at which the amplifier enters infinite compression.

In a preferred embodiment of the above aspects of the invention, the slope of the amplifier response in the dynamic range can be adjusted in response to a change in the monitored level of background noise. In one embodiment, the slope of the amplifier response can be decreased in response to a decrease in the monitored level of background noise. For example, at a predetermined level of background noise, that hereinafter is called a "moderate" level of background noise, the gain can be set to a ratio of about 1:1 across the dynamic range. At times when the level of background noise is less than the predetermined "moderate" level, the gain can be set to a ratio of about 2:1 across the dynamic range. Other ratios, both between and outside the above values can be envisaged.

In a further embodiment of the above aspects, the input signal level at which the amplifier enters infinite compression is the same irrespective of the slope of the gain of the amplifying means. That is, while a change in current estimated noise floor value causes a change in the level at which an input signal is amplified to produce an output signal at a level equal to the hearing threshold value, the slope of the amplifier response in the dynamic range is controlled by the gain control means such that the input signal level at which the amplifier enters infinite compression remains the same, despite the change in current estimated noise floor value.

In a further embodiment, the slope of the amplifier response in the dynamic range can be non-linear. The non-linearity of the slope of the amplifier response in the dynamic range can vary in response to changes in the current estimated noise floor value.

In yet another embodiment, the slope of the amplifier response, with increasing input signal level, can be linear at a first ratio to a breakpoint and then be linear at a second ratio different to the first ratio, until infinite compression. It will be appreciated that a second or greater number of breakpoints could also be utilised.

In such embodiments, the slope of the amplifier response is preferably greater for smaller input signal levels, and is reduced for input signal levels above the breakpoint or first breakpoint. Hence, input signals such as speech received at levels above the breakpoint will be partially compressed, relative to input signals at a level below the breakpoint. Such compression can improve understanding of speech for cochlear implant users, which may be attributable to the broad dynamic range of the amplifier provided by such embodiments.

In such embodiments, the position of the breakpoint preferably varies in response to changes in the current estimated noise floor value. In a preferred embodiment, the first ratio is 1:1 and the second ratio is 2:1. Other ratios both between and outside these ranges of variation can be envisaged.

In a preferred embodiment, the lower the current estimated noise floor value, the lower the breakpoint between the first and second ratios. In this case, more of the input signal is subject to a 2:1 compression than is the case when the higher current estimated noise floor value is at a higher level. As the current estimated noise floor value increases, the region occupied by the 2:1 slope between the threshold and infinite compression decreases. When the current estimated noise floor level reaches a predetermined level of background noise, the slope has no breakpoint between the two ratios and simply has a linear fixed ratio before reaching infinite compression.

While it will normally be desirable to ensure that the output signal never exceeds the maximum comfort level, it should be appreciated that, in certain instances, the amplifier response may extend above the maximum comfort level. This may be particularly useful where a user is having a problem in monitoring the loudness of their own voice.

In one embodiment, the current estimated noise floor value is determined by tracking the lowest signal level observed in the input signal over a preceding period of time, such as a number of seconds. By observing the input signal level over a number of preceding seconds, this determination of the current estimated noise floor value allows for natural breaks in conversation, during which the input signal level is assumed to equal the noise floor. If a new lower level is detected, the current estimated noise floor value is updated to the lower level. However, if for some predetermined period of time, the noise is above the lowest observed, the noise floor estimate is gradually increased.

In one embodiment, the gain control means is implemented using software executed by a microcontroller.

In a preferred embodiment, the present invention can be applied to the complete signal or separately to specific parts of the signal. In applications where the signal is bandpass filtered, and broken into separate ranges of frequencies, it is envisaged that the present invention could be applied to all frequency bands or separately to bands of high or low frequencies as would be applicable to the desired application.

BRIEF DESCRIPTION OF DRAWINGS

By way of example only, preferred embodiments of the invention are described with reference to the accompanying drawings, in which.

DESCRIPTION OF THE INVENTION

Figure 1:
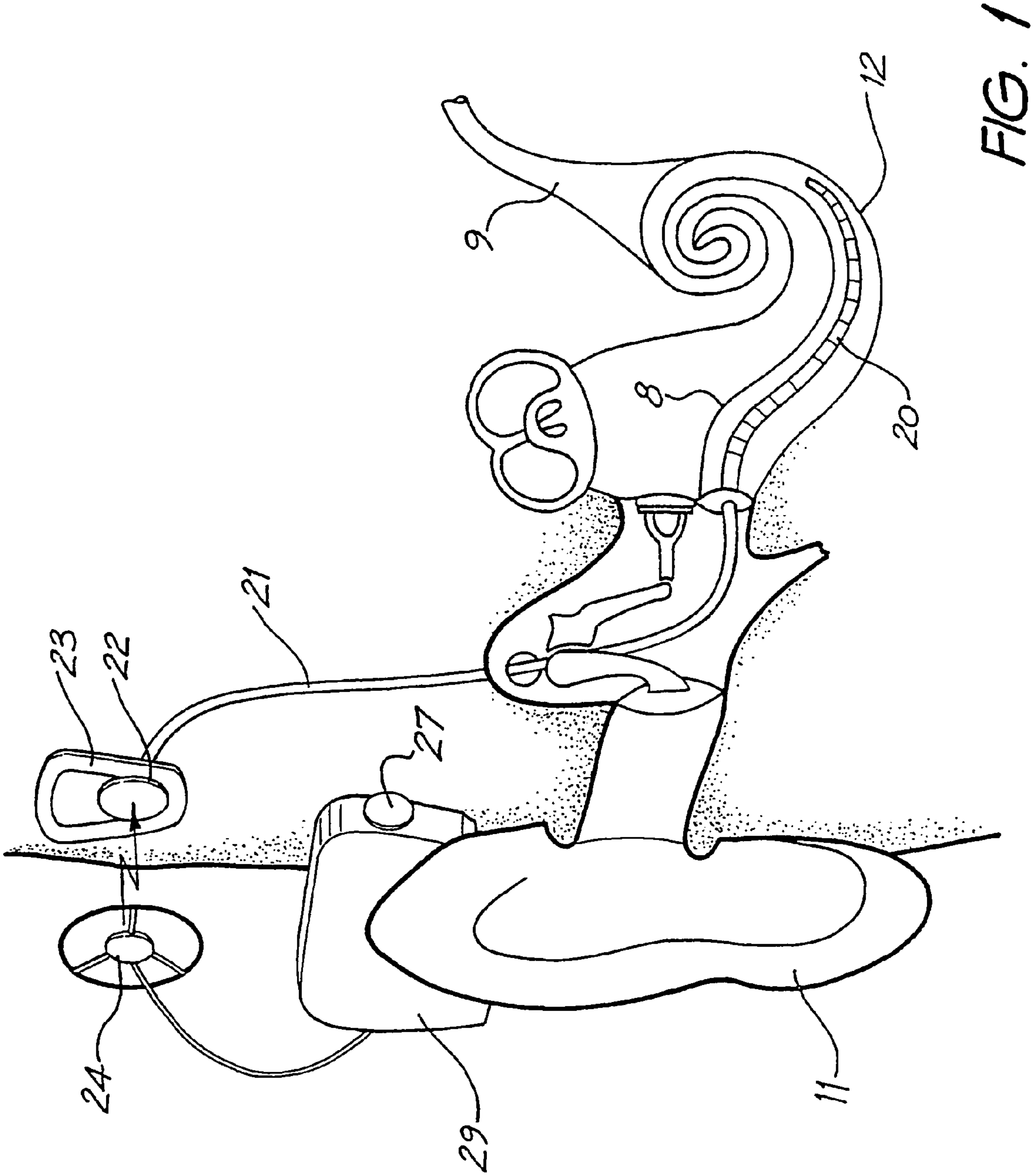
FIG. 1 is a pictorial representation of a prior art cochlear implant system.

Before describing the features of the present invention, it is appropriate to briefly describe the construction of one type of known cochlear implant system with reference to FIG. 1.

Known cochlear implants typically consist of two main components, an external component including a speech processor 29, and an internal component including an implanted receiver and stimulator unit 22. The external component includes an on-board microphone 27. The speech processor 29 is, in this illustration, constructed and arranged so that it can fit behind the outer ear 11. Alternative versions may be worn on the body. Attached to the speech processor 29 is a transmitter coil 24 which transmits electrical signals to the implanted unit 22 via an RF link.

The implanted component includes a receiver coil 23 for receiving power and data from the transmitter coil 24. A cable 21 extends from the implanted receiver and stimulator unit 22 to the cochlea 12 and terminates in an electrode array 20. The signals thus received are applied by the array 20 to the basilar membrane 8 thereby stimulating the auditory nerve 9. The operation of such a device is described, for example, in U.S. Pat. No. 4,532,930.

The sound processor 29 of the cochlear implant can perform an audio spectral analysis of the acoustic signals and outputs channel amplitude levels. The sound processor 29 can also sort the outputs in order of magnitude, or flag the spectral maxima as used in the SPEAK strategy developed by Cochlear Ltd.

Figure 2:
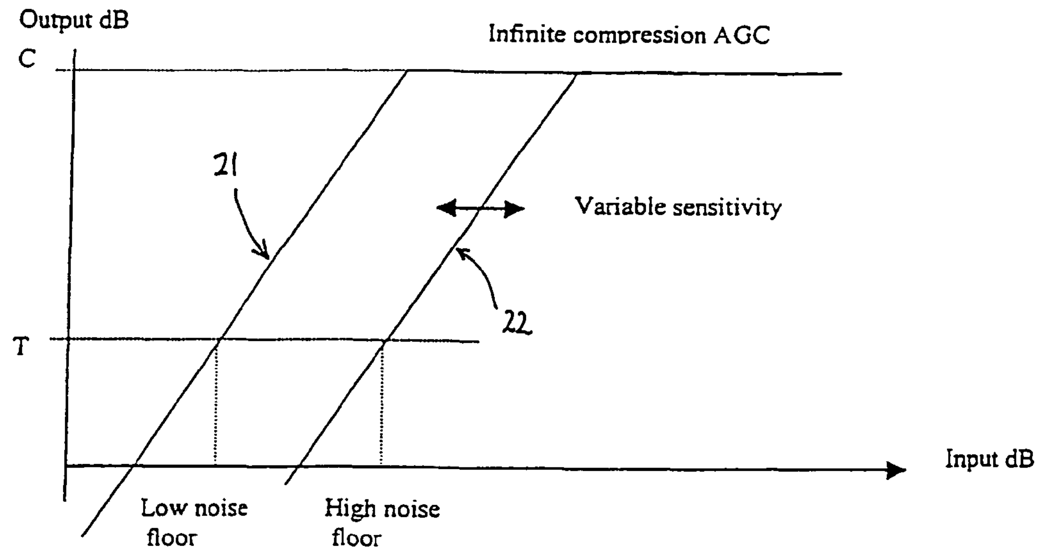
FIG. 2 is an example of a prior art Automatic Gain Control with Automatic Sensitivity Control

FIG. 2 depicts a prior art AGC in use with normal sensitivity control, under two different noise floor conditions. The two points on the vertical axis of the graph referred to as T and C correspond to the user's Threshold Level and the user's Comfort level. The Threshold level refers to the smallest amount of sound that the user is able to hear and the Comfort level is the upper limit of sound that the user can experience which does not produce an uncomfortably loud sensation.

In a first instance, a low noise floor level is present, and the response of the AGC is indicated by the left hand locus 21. In the second instance, a higher noise floor level is present, with the response of the AGC being indicated by the right hand locus 22. In both these different noise floor conditions the sensitivity has been adjusted so that the threshold level corresponds approximately to the determined noise floor level. Essentially the sensitivity setting determines when the AGC will become active and in both these instances, the AGC becomes active as soon as the sound goes above the noise floor level.

In both these conditions a linear gain is applied to the input signal between the T and C output levels with the amount of gain being constant in each instance, as can be seen by the gradient of each locus. That is, the higher gain in the first instance is the same for both low input signal levels and high input signal levels, and similarly, the lower gain in the second instance is the same for both low input signal levels and high input signal levels. In the first instance (in which a lower noise floor is present) the gain applied to the input signal is relatively higher, to ensure the AGC becomes active as soon as the input sound goes above the noise floor level. Conversely, in the second instance (when a relatively higher noise floor level is present), the gain applied to the input signal is relatively lower, again to ensure that the AGC becomes active as the input sound goes above the noise floor level. In both cases, infinite compression of the input signal occurs when the output signal is at the C level such that any further increase in the input signal level results in an equivalent gain reduction to keep the output level stable. For each of the two situations the essential difference in the action of the AGC is the point of onset of the AGC. It can be seen that the dynamic range of the AGC remains the same in each instance.

Figure 3:
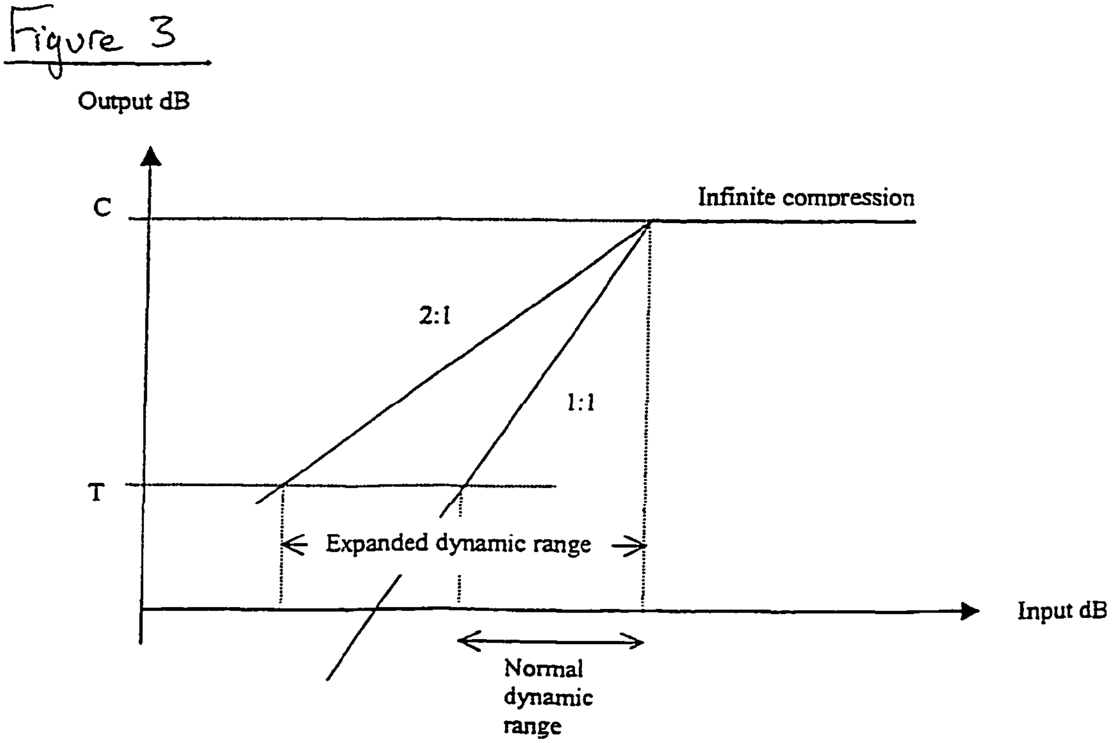
FIG. 3 is an example of an Adaptive Variable Slope Automatic Gain Control in accordance with the present invention.

FIG. 3 depicts the gain of an amplifier according to the present invention used in an auditory prosthesis, such as the cochlear implant depicted in FIG. 1. Review of the graph reveals a similar aspect to FIG. 2, in that the amplifier has a linear gain from a relatively low output signal level (threshold T) to a maximum output level at infinite compression C. In using an amplifier having a gain control operating as depicted in FIG. 3, a noise floor estimate is used to determine a lower point through which the slope passes. An upper point of the slope is fixed, and defined by the input signal threshold $In_{max}$ at which infinite compression occurs. As the noise floor level increases, the gradient of the slope changes to a higher gradient in a manner such that the dynamic input range is reduced, resulting in input signals below the noise floor not being amplified above threshold T, and signals above the noise floor being amplified by a lesser amount than would be the case for a lower noise floor level, leading to a steeper slope of the AGC response. Therefore, by monitoring the change in the noise floor level, the amplifier according to the present invention applies a differing amount of gain to the input signal, tailored to meet the specific requirements of the sound environment. In other words, the noise floor estimate is used to set the slope of the AGC response so that the lower end of the AGC response is adjusted to correspond to the determined noise floor.

Figure 4:
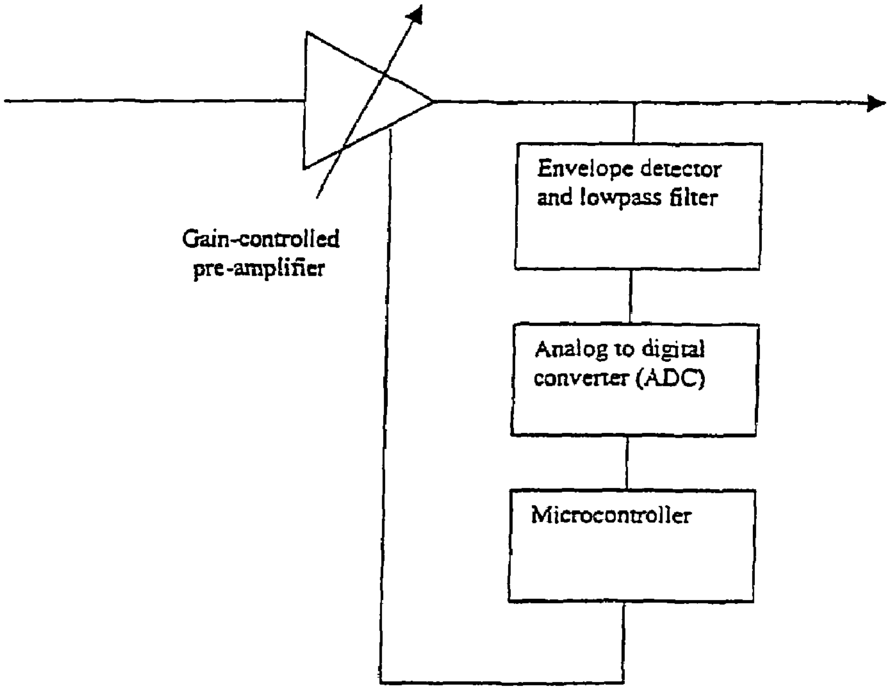
FIG. 4 is an example of a control algorithm for an Adaptive Variable Slope Automatic Gain Control.
Figure 5:
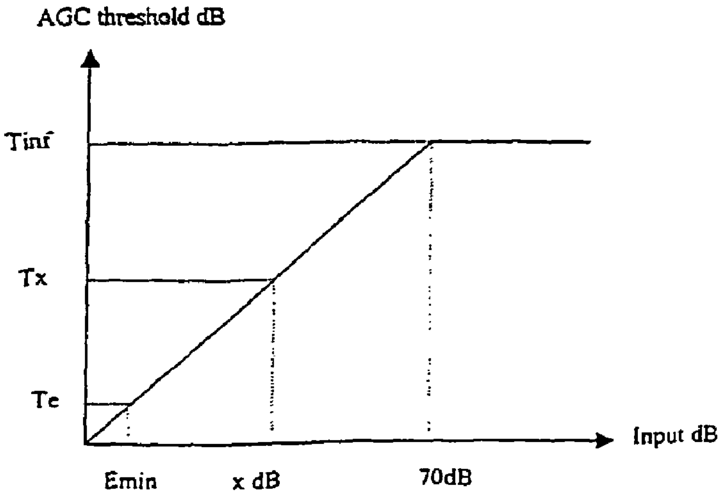
FIG. 5 is an illustration of the threshold in an Adaptive Variable Slope Automatic Gain Control.

The gain control depicted by FIG. 3 can be implemented, in one embodiment, using software in a microcontroller (such as is depicted in FIGS. 4 and 5). In this case, a measurement of the signal amplitude at the output of the gain controlled amplifier is taken where the signal is conveniently high. The input signal is then calculated using the known gain set in the amplifier. This is then used to determine the noise floor estimate and as the noise floor varies, the amplifier response is varied in a manner such that input signals at a level equal to the current estimated noise floor value are magnified to an output signal equal to the hearing threshold level T, and the slope of the amplifier response is controlled so that the amplifier response always enters infinite compression at the same point (where the input signal is at, for example, 70 dB as in FIG. 5).

To achieve this, an output signal level Tx. for an arbitrary input level x dB (Decibels) (as shown in FIG. 5), can be calculated by means of the equation:

$$Tx=x^*(T\text{inf}-Te)/(70-E\text{min}).$$

Tinf is the threshold for infinite compression, corresponding to C. Te is the threshold required to result in an audible (T level) stimulation, x dB is an arbitrary input level, Emin is the floor noise level and 70 dB is an example of a fixed input signal threshold at which the amplifier response enters infinite compression.

Figure 6:
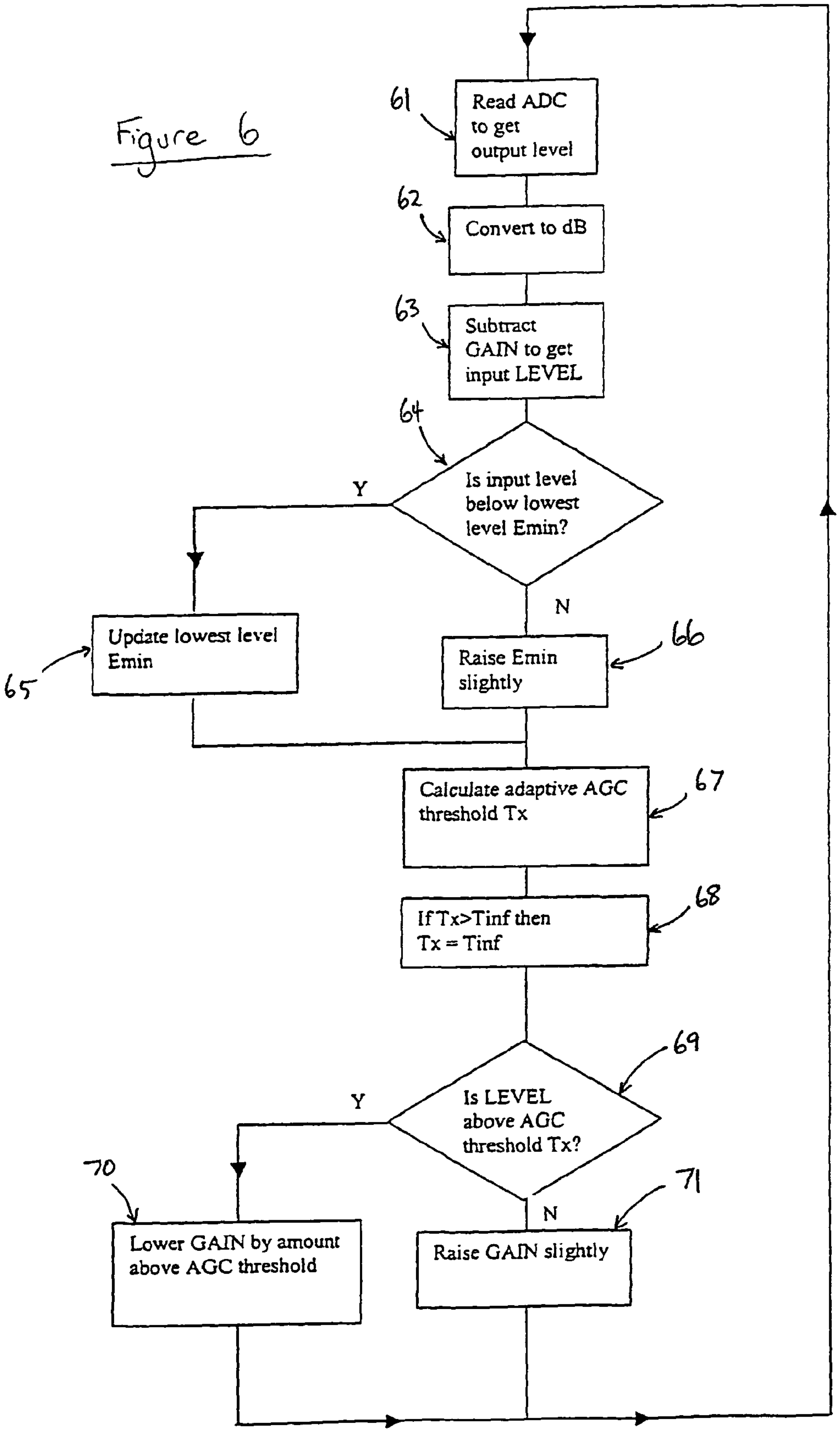
FIG. 6 is an example of an iterative feedback control algorithm for an Adaptive Variable Slope Automatic Gain Control.

An iterative feedback algorithm can be used to implement this control procedure (such as that depicted in FIG. 6). As noted above, a level of the output signal is first determined at steps 61 and 62. From that output signal level, the input signal level is then determined by subtracting the gain of the amplifier, at 63. At 64, the determined input level is compared to the lowest level Emin, which is a comparison of the current estimated noise floor value (Emin) with the actual measured input signal level. If the actual input signal level is lower than Emin, the current estimated noise floor level (Emin) is immediately updated to that lower level (at step 65). It can be seen that the “release” time of the current estimated noise floor value (Emin) is essentially zero. On the other hand, if the measured input signal level is greater than the current estimated noise floor value (Emin), the current estimated noise floor value (Emin) is raised slightly (at 66). As noted previously, the “attack” time of the current estimated noise floor value is slow, typically of the order of five to ten seconds. A slow attack time compensates for those periods in which the input signal level is above the true noise floor, for example when human speech is received by the cochlear implant.

Output signal level Tx is then calculated as discussed above with reference to FIG. 5 (at 67 and 68). Finally, at steps 69 to 71, the adaptive gain is implemented, having a fast attack time (refer to 70), and a relatively slow release time (refer to 71).

Figure 7:
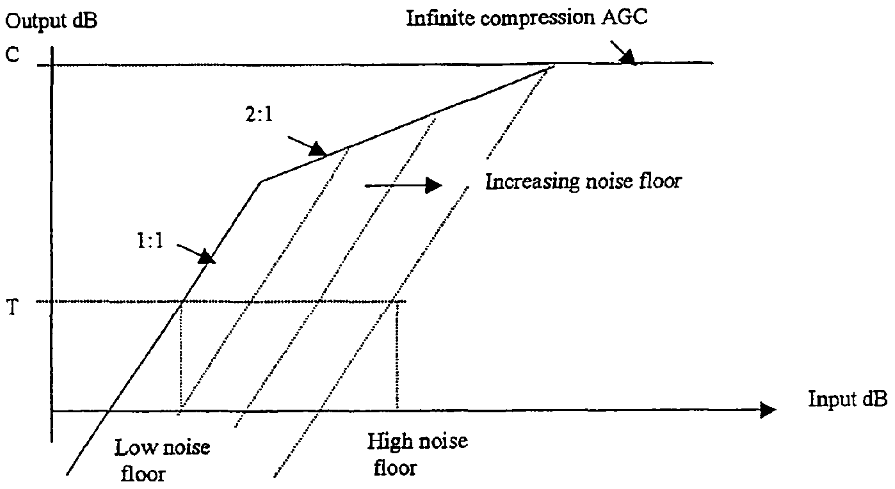
FIG. 7 is an example of a combination of an Automatic Sensitivity Control and an Automatic Gain Control.

An alternative gain control method in accordance with the present invention is represented in FIG. 7. In this embodiment, rather than adjusting the slope of the gain in accordance with the change in the noise floor level, a point at which the slope of the AGC response changes can be adjusted. The slope of the response of the amplifier in this embodiment is linear at a first ratio to a breakpoint and is then linear at a second ratio different to the first ratio until infinite compression commences.

In this embodiment, the position of the breakpoint preferably varies in response to changes in the monitored level of background noise. In the depicted embodiment, the first ratio is 1:1 and the second ratio is 2:1. Other ratios both between and outside these ranges of variation can be envisaged and also it is envisaged that there could be more than one breakpoint between more than two ratios.

The lower the monitored noise floor level, the lower the breakpoint between the first and second ratios. In this case, more of the input signal is subject to a 2:1 compression than is the case at relatively higher monitored noise floor levels. As the monitored noise floor level increases, the region occupied by the 2:1 slope between the threshold and infinite compression decreases. At a predetermined noise floor level, the slope has no breakpoint between the two ratios and simply has a linear fixed ratio before reaching infinite compression.

Each of the parallel lines in FIG. 7 corresponds to a particular level of the background noise, the noise floor. The parallel lines all have a slope of 1:1 in this example, meaning that, on each line no compression is applied when the input signal level is between threshold T and the infinite compression level C. Each of these lines intersects either the line indicating levels for which compression of 2:1 is applied, or the horizontal line, which indicates levels at which infinite compression is applied.

Below the breakpoint indicated in FIG. 6, linear amplification is applied to input signals, while above the breakpoint, compression with a ratio of 2:1 is applied. In the present embodiment, the effective breakpoint varies in response to changes in the estimated level of background noise. Specifically, the breakpoint is increased automatically as the noise floor increases. The breakpoint will remain on the line of 2:1 compression, and approaches the point of infinite compression as the noise floor increases from low values.

Figure 8:
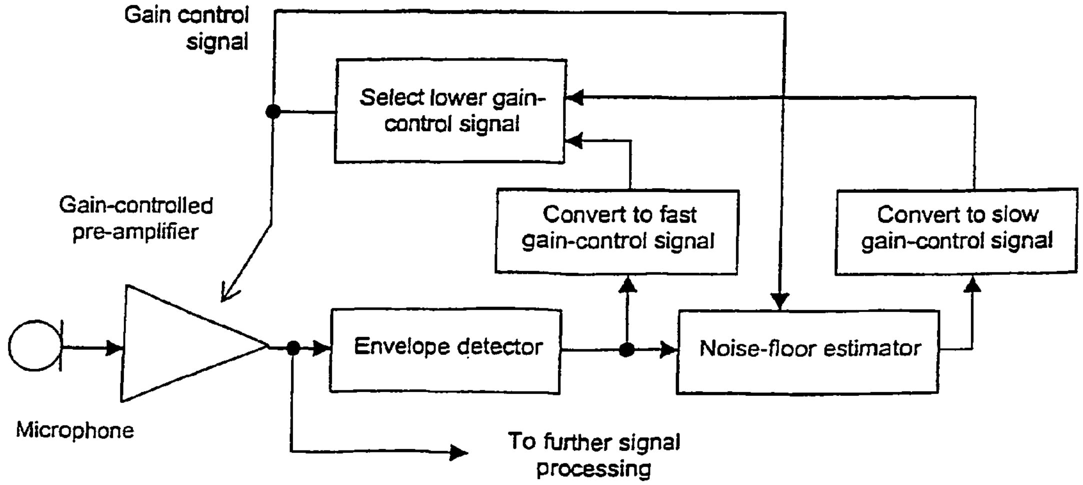
FIG. 8 is an example of a control system for an Automatic Sensitivity Control and an Automatic Gain Control.

An example of how this method may be implemented in practice is shown in a block diagram (FIG. 8). Incoming sounds are detected by a microphone and converted into analog electric signals. These signals are amplified by a preamplifier with gain determined by a gain control signal. The amplified signals pass into an envelope detector. The output of the envelope detector is processed to provide a running estimate of the noise floor level. In addition, the output of the envelope detector is converted into a fast-acting gain-control signal which if applied directly to the gain-controlled preamplifier, would compress the input signal by a ratio of 2:1. The estimate of the noise floor is converted into a second gain-control signal which if applied directly to the gain-controlled preamplifier, would cause the background noise to be amplified to a level close to or slightly above the level producing electric stimulation at the T level. The rate of change of the gain-control signal derived from the estimated noise floor is much slower than the rate of change of the gain-control signal derived from the envelope detector. At any instant of time, only one of these two gain-control signals is applied to the pre-amplifier. The selected gain-control signal is always that which results in the lower of the two possible pre-amplifier gains. The gain-control signal currently applied to the pre-amplifier is passed to the noise-floor estimator. This enables the noise-floor estimator to compensate for the particular gain being applied to the microphone signal at all times, so that the estimate refers to the level of noise actually detected by the microphone. Alternatively, the noise-floor estimator may obtain its input signal from the microphone via a separate, fixed-gain pre-amplifier. Further to this, an alternative implementation of the noise-floor estimator may be to generate a signal that tracks the temporal minima in the waveform produced by the envelope detector. For example, when the output of the envelope detector is below the current noise-floor estimate, the noise-floor estimate may be rapidly reduced to equal the envelope level. When the output of the envelope detector is above the current noise-floor estimate, the noise-floor estimate may increase slowly in level. The envelope detector may have an attack time, the time taken for the gain to decrease in response to an increase in the background noise level, of less than 5 ms and a release time of about 50 ms. For the noise-floor estimator, the attack time may be about 10 seconds, while the release time may be near zero.

Figure 9:
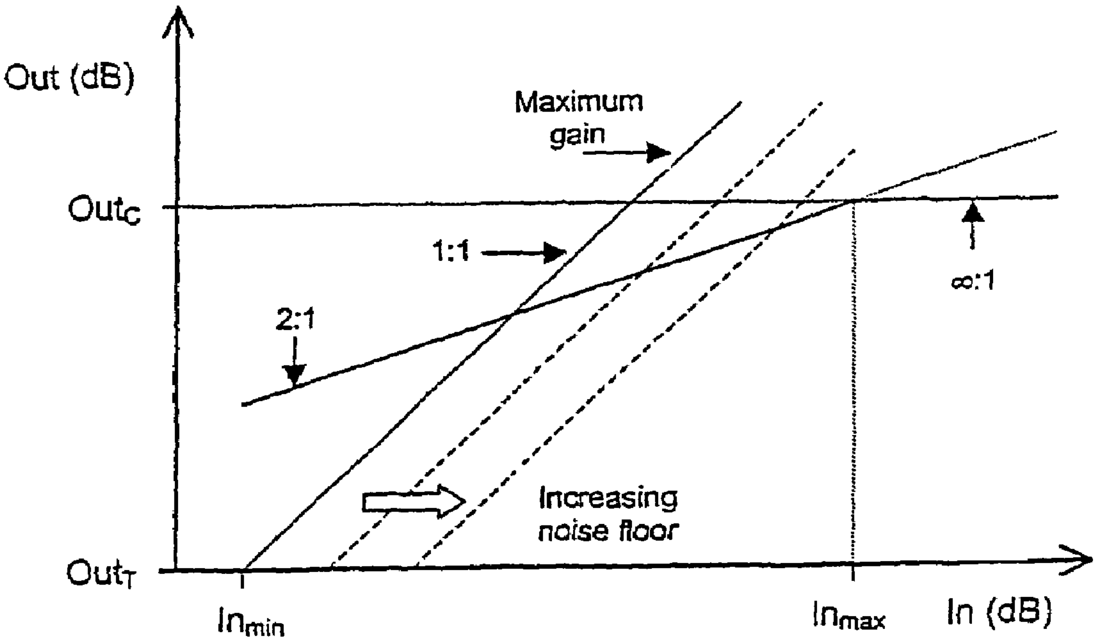
FIG. 9 is an example of a combination of an Automatic Sensitivity Control and an Automatic Gain Control.

FIG. 9 provides a depiction of the principle of operation of this method. Shown is the relationship between the input (In) and output (Out) signals of the entire AGC scheme for various conditions. $In_{min}$ and $In_{max}$ are the minimum and maximum sound pressure levels referred to the microphone input of the speech processor. Typically, $In_{max}$ is about 70 dB SPL, and $In_{min}$ is determined by the electrical noise level internal to the speech-processor circuitry. $Out_T$ and $Out_C$ are the signal levels produced by the AGC circuit that result in electric stimulation at the T-level and C-level, respectively. MaximumGain refers to the line on which an input at $In_{min}$, the internal noise level, produces an output of $Out_T$, causing T-level stimulation. The lines labelled 1:1, 2:1, and ∞:1 represent linear amplification, 2:1 compression, and infinite compression limiting, respectively. The parallel lines represent different linear gains based on the estimated level of the noise floor. These gains reduce, below MaximumGain, for increasing noise-floor levels, represented on the diagram by a shift of the 1:1 line to the right.

The operation of the embodiment illustrated in FIG. 9 may be summarised by the following equation:

$$Gain_{AGC}=\text{Minimum}(\text{MaximumGain}, Gain_F, Gain_L, Gain_S)$$

where:

1) MaximumGain is as described above;

2) $Gain_F$ corresponds to the line having 2:1 compression ratio, with a compression threshold of zero, a compression ratio of 2:1, and fast (syllabic) time constants. This gain is based on the short-term amplitude of the input-signal level (In) by:

$$Gain_F=Out_C-(In_{max}/2)-(In/2);$$

3) $Gain_S$ defines the parallel lines having 1:1 compression ratio which adjust to noise floor changes (ie: a noise-floor tracker), having a compression threshold of $In_{min}$, a 1:1 compression ratio, slow time constants, the gain, Gains, is based on the estimated level of the noise floor, NF, by:

$$Gain_S=MaximumGain+In_{min}-NF(NF\geqq In_{min});\text{ and}$$

4) $Gain_L$ provides the infinite compression for high input signal levels, (ie acts as a limiter), with a compression threshold of $In_{max}$, an infinite compression ratio, fast time constants, the gain, $Gain_L$, is based on the short-term amplitude of the input-signal level (In) such that, if In is greater than $In_{max}$, then:

$$Gain_L=Out_C-In.$$

Hence, the overall gain, $Gain_{AGC}$, of the entire system at any time is the minimum of the above gain values.

The implementation of the current embodiment provides that speech or other sounds received at a relatively high level are compressed using a moderate compression ratio, for example 2:1, and short time constants, improving the understanding of speech for users of hearing devices. The level of background noise is tracked relatively slowly by the noise-floor estimator, and is used to set the pre-amplifier gain such that the noise will usually be perceived as comparatively soft by device users, avoiding the problem of background noise being perceived to have excessive loudness when a progressive compressor with a fixed compression ratio is used in a hearing device speech processor. Excessive sound levels always receive infinite compression, and are converted to electric stimulation at the C-level, so they should never be perceived to have uncomfortable loudness. The implementation is efficient and is based on a small number of previously developed signal processing functions.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An amplifier for providing adaptive operation of an auditory prosthesis, the amplifier operable to receive an input signal and produce an output signal, the amplifier comprising:

a gain controller having a gain response to be applied to the input signal to produce the output signal; and a noise floor estimator for providing a current estimated noise floor value of the input signal, wherein, in response to a change in the current estimated noise floor value, the gain controller is operable to alter the gain response of the gain controller and to alter an input dynamic range of the gain controller, the input dynamic range being between a minimum threshold value of the input signal and a maximum threshold value of the input signal.

2. The amplifier of claim 1 wherein the current estimated noise floor value is derived from the input signal.

3. The amplifier of claim 1 or claim 2 wherein the current estimated noise floor value is substantially continuously updated.

4. The amplifier of claim 1 or claim 2 wherein the current estimated noise floor value is periodically updated.

5. The amplifier of claim 2 wherein the current estimated noise floor value is derived from the input signal by monitoring an envelope of the input signal and determining the current estimated noise floor value based on detected minima of that envelope.

6. The amplifier of claim 1 wherein the amplifier gain varies for differing input signal levels.

7. The amplifier of claim 6 wherein alteration of the amplifier response in the dynamic range responsive to a varying noise floor level is implemented to adapt to an individual user's requirements.

8. The amplifier of claim 1 wherein the amplifier response is continuous, monotonic and increasing for all output signal levels between a hearing threshold value of a user and a maximum comfort value of the user.

9. The amplifier of claim 1 wherein the amplifier produces an output signal substantially equal in magnitude to the hearing threshold value of a user when the input signal is substantially equal to the current estimated noise floor level.

10. The amplifier of claim 1 wherein the gain controller ensures that the amplifier does not produce any output signals which exceed a maximum comfort level of a user.

11. The amplifier of claim 10 wherein the amplifier produces a constant output signal level for all input signal levels above a maximum input level.

12. The amplifier of claim 11 wherein the maximum input level is in the range 60-90 dB.

13. The amplifier of claim 10 wherein the maximum input level is substantially 70 dB.

14. The amplifier of claim 1 wherein the gain controller controls the amplifier to have a substantially zero gain for input signals below the current estimated noise floor value, such that substantially no output signal is produced when input signals at such levels are received by the amplifier.

15. The amplifier of claim 1 wherein the gain controller controls the amplifier to have a substantially constant gain for input signals below the current estimated noise floor value.

16. The amplifier of claim 1, wherein the amplifier is for providing adaptive operation of a hearing aid.

17. The amplifier of claim 1, wherein the amplifier is for providing adaptive operation of a cochlear implant.

18. The amplifier of claim 1, wherein the amplifier provides linear gain of input signals which are greater in amplitude than the current estimated noise floor value, and are lesser in amplitude than an input signal level at which the amplifier enters infinite compression.

19. The amplifier of claim 1 wherein a slope of the amplifier response in the dynamic range of the amplifier can be adjusted in response to a change in the current estimated noise floor value.

20. The amplifier of claim 19 wherein the slope of the amplifier response is decreased in response to a decrease in the monitored level of background noise.

21. The amplifier of claim 1 wherein an input signal level at which the amplifier enters infinite compression is the same irrespective of the slope of the gain of the amplifying means.

22. The amplifier of claim 1 wherein a slope of the amplifier response in the dynamic range is non-linear.

23. The amplifier of claim 22 wherein the non-linearity of the slope of the amplifier response in the dynamic range varies in response to changes in the current estimated noise floor value.

24. The amplifier of claim 1 wherein the amplifier is capable of being controlled to produce an output signal greater than a maximum comfort level of a user.

25. The amplifier of claim 1 wherein the current estimated noise floor value is determined by monitoring a lowest signal level observed in the input signal within a preceding period of time.

26. The amplifier of claim 25 wherein the period of time is of the order of seconds, to allow for natural breaks in conversation.

27. The amplifier of claim 25 or 26 wherein, if an observed lowest signal level in the preceding period of time is lower than the current estimated noise floor value, the current estimated noise floor value is changed to the new lower level.

28. The amplifier of claim 25 wherein, if an observed lowest signal level in the preceding period of time is greater than the current estimated noise floor value, the current noise floor estimate is increased fractionally towards the observed lowest signal level.

29. The amplifier of claim 1 wherein the gain controller is implemented using software executed by a microcontroller.

30. An amplifier for providing adaptive operation of an auditory prosthesis, the amplifier operable to receive an input signal and produce an output signal, the amplifier comprising:

a gain control means; and means to provide a current estimated noise floor value of the input signal, wherein, in response to a change in the current estimated noise floor value, the gain control means is operable to alter the amount of gain applied to the input signal and wherein a dynamic range of the amplifier is increased in response to a decrease in the current estimated noise floor value.

31. An amplifier for providing adaptive operation of an auditory prosthesis, the amplifier operable to receive an input signal and produce an output signal, the amplifier comprising:

a gain control means; and means to provide a current estimated noise floor value of the input signal, wherein, in response to a change in the current estimated noise floor value, the gain control means is operable to alter the amount of gain applied to the input signal and wherein a dynamic range of the amplifier is decreased in response to an increase in the current estimated noise floor value.

32. An amplifier for providing adaptive operation of an auditory prosthesis, the amplifier operable to receive an input signal and produce an output signal, the amplifier comprising:

a gain control means; and means to provide a current estimated noise floor value of the input signal, wherein, in response to a change in the current estimated noise floor value, the gain control means is operable to alter the amount of gain applied to the input signal, wherein a slope of the amplifier response in the dynamic range of the amplifier can be adjusted in response to a change in the current estimated noise floor value, and wherein, at a perceived moderate level of background noise, the gain of the amplifier is set to a ratio of substantially 1:1 across the dynamic range.

33. The amplifier of claim 32 wherein, when the level of background noise is less than the perceived moderate level, the gain is set to a ratio of substantially 2:1 across the dynamic range.

34. An amplifier for providing adaptive operation of an auditory prosthesis, the amplifier operable to receive an input signal and produce an output signal, the amplifier comprising:

a gain control means; and means to provide a current estimated noise floor value of the input signal, wherein, in response to a change in the current estimated noise floor value, the gain control means is operable to alter the amount of gain applied to the input signal, wherein a slope of the amplifier response in the dynamic range is non-linear, and wherein, with increasing input signal level, the slope of the amplifier response in the dynamic range is linear at a first ratio to a breakpoint and then linear at a second ratio different to the first ratio, until infinite compression.

35. The amplifier of claim 34 wherein a plurality of breakpoints occur across the dynamic range of the amplifier.

36. The amplifier of claim 34 wherein the slope of the amplifier response is greater for smaller input signal levels, and is reduced for input signal levels above the breakpoint or first breakpoint, such that input signals received at levels above the breakpoint will be partially compressed, relative to input signals at a level below the breakpoint.

37. The amplifier of claim 34 wherein a position of the breakpoint within the dynamic range varies in response to changes in the current estimated noise floor value.

38. The amplifier of claim 34 wherein the first ratio is substantially 1:1 and the second ratio is substantially 2:1.

39. An amplifier for providing adaptive operation of an auditory prosthesis, the amplifier operable to receive an input signal and produce an output signal, the amplifier comprising:

a gain control means; and means to provide a current estimated noise floor value of the input signal, wherein, in response to a change in the current estimated noise floor value, the gain control means is operable to alter the amount of gain applied to the input signal, and wherein, in response to a change in the current estimated noise floor value, the gain control means is operable to alter a gain compression ratio of the amplifier across at least a portion of the dynamic range of the amplifier.

40. The amplifier of claim 39 wherein the current estimated noise floor value is derived from the input signal.

41. The amplifier of claim 39 or claim 40 wherein the current estimated noise floor value is substantially continuously updated.

42. The amplifier of claim 39 or claim 40 wherein the current estimated noise floor value is periodically updated.

43. The amplifier of claim 40 wherein the current estimated noise floor value is derived from the input signal by monitoring an envelope of the input signal and determining the current estimated noise floor value based on detected minima of that envelope.

44. The amplifier of claim 39 wherein alteration of the gain compression ratio of the amplifier is implemented to adapt to an individual user's requirements.

45. The amplifier of claim 39 wherein a dynamic range of the amplifier is increased in response to a decrease in the current estimated noise floor value.

46. The amplifier of claim 39 wherein a dynamic range of the amplifier is decreased in response to an increase in the current estimated noise floor value.

47. The amplifier of claim 39 wherein the amplifier response is continuous, monotonic and increasing for all output signal levels between a hearing threshold value of a user and a maximum comfort value of the user.

48. The amplifier of claim 39 wherein the amplifier produces an output signal substantially equal in magnitude to the hearing threshold value of a user when the input signal is substantially equal to the current estimated noise floor level.

49. The amplifier of claim 39 wherein the gain control means ensures that the amplifier does not produce any output signals which exceed a maximum comfort level of a user.

50. The amplifier of claim 49 wherein the amplifier produces a constant output signal level for all input signal levels above a maximum input level.

51. The amplifier of claim 50 wherein the maximum input level is in the range 60-90 dB.

52. The amplifier of claim 51 wherein the maximum input level is substantially 70 dB.

53. The amplifier of claim 39 wherein the gain control means controls the amplifier to have a substantially zero gain for input signals below the current estimated noise floor value, such that substantially no output signal is produced when input signals at such levels are received by the amplifier.

54. The amplifier of claim 39 wherein the gain control means controls the amplifier to have a substantially constant gain for input signals below the current estimated noise floor value.

55. The amplifier of claim 39, wherein the amplifier is for providing adaptive operation of a hearing aid.

56. The amplifier of claim 39, wherein the amplifier is for providing adaptive operation of a cochlear implant.

57. The amplifier of claim 39 wherein a slope of the amplifier response in the dynamic range of the amplifier is decreased in response to a decrease in the monitored level of background noise.

58. The amplifier of claim 57 wherein, at a perceived moderate level of background noise, the gain compression ratio of the amplifier is set to substantially 1:1 across the dynamic range.

59. The amplifier of claim 58 wherein, when the level of background noise is less than the perceived moderate level, the gain compression ratio is set to substantially 2:1 across the dynamic range.

60. The amplifier of claim 39 wherein an input signal level at which the amplifier enters infinite compression is the same irrespective of the slope of the gain of the amplifying means.

61. The amplifier of claim 60 wherein, if an observed lowest signal level in the preceding period of time is greater than the current estimated noise floor value, the current noise floor estimate is increased fractionally towards the observed lowest signal level.

62. The amplifier of claim 39 wherein a slope of the amplifier response in the dynamic range is non-linear.

63. The amplifier of claim 62 wherein the non-linearity of the slope of the amplifier response in the dynamic range varies in response to changes in the current estimated noise floor value.

64. The amplifier of claim 62 or claim 63 wherein, with increasing input signal level, the slope of the amplifier response in the dynamic range is linear at a first ratio to a breakpoint and then linear at a second ratio different to the first ratio, until infinite compression.

65. The amplifier of claim 64 wherein a plurality of breakpoints occur across the dynamic range of the amplifier.

66. The amplifier of claim 64 wherein the slope of the amplifier response is greater for smaller input signal levels, and is reduced for input signal levels above the breakpoint or first breakpoint, such that input signals received at levels above the breakpoint will be partially compressed, relative to input signals at a level below the breakpoint.

67. The amplifier of claim 64 wherein a position of the breakpoint within the dynamic range varies in response to changes in the current estimated noise floor value.

68. The amplifier of claim 64 wherein the first ratio is substantially 1:1 and the second ratio is substantially 2:1.

69. The amplifier of claim 39 wherein the amplifier may be controlled to produce an output signal greater than a maximum comfort level of a user.

70. The amplifier of claim 39 wherein the current estimated noise floor value is determined by monitoring a lowest signal level observed in the input signal within a preceding period of time.

71. The amplifier of claim 70 wherein the period of time is of the order of seconds, to allow for natural breaks in conversation.

72. The amplifier of claim 70 or claim 71 wherein, if an observed lowest signal level in the preceding period of time is lower than the current estimated noise floor value, the current estimated noise floor value is changed to the new lower level.

73. The amplifier of claim 39 wherein the gain control means is implemented using software executed by a microcontroller.

74. An amplifier for providing adaptive operation of an auditory prosthesis, the amplifier operable to receive an input signal and produce an output signal, the amplifier comprising a gain control means, wherein the gain control means is operable to control the gain of the amplifier in response to a current estimated noise floor value such that the amplifier will only produce an output signal which is greater than or substantially equal to a hearing threshold value when the input signal of the amplifier is greater than or substantially equal to the current estimated noise floor value, and wherein the gain control means is operable to alter the dynamic range of the amplifier in response to a change in the current estimated noise floor value.

75. The amplifier of claim 74 wherein the current estimated noise floor value is derived from the input signal.

76. The amplifier of claim 74 or claim 75 wherein the current estimated noise floor value is substantially continuously updated.

77. The amplifier of claim 74 or claim 75 wherein the current estimated noise floor value is periodically updated.

78. The amplifier of claim 75 wherein the current estimated noise floor value is derived from the input signal by monitoring an envelope of the input signal and determining the current estimated noise floor value based on detected minima of that envelope.

79. The amplifier of claim 74 wherein the amplifier gain varies for differing input signal levels.

80. The amplifier of claim 79 wherein alteration of the amplifier response in the dynamic range responsive to a varying noise floor level is implemented to adapt to an individual user's requirements.

81. The amplifier of claim 74 wherein a dynamic range of the amplifier is increased in response to a decrease in the current estimated noise floor value.

82. The amplifier of claim 74 wherein a dynamic range of the amplifier is decreased in response to an increase in the current estimated noise floor value.

83. The amplifier of claim 74 wherein the amplifier response is continuous, monotonic and increasing for all output signal levels between a hearing threshold value of a user and a maximum comfort value of the user.

84. The amplifier of claim 74 wherein the amplifier produces an output signal substantially equal in magnitude to the hearing threshold value of a user when the input signal is substantially equal to the current estimated noise floor value.

85. The amplifier of claim 74 wherein the gain control means ensures that the amplifier does not produce any output signals which exceed a maximum comfort level of a user.

86. The amplifier of claim 85 wherein the amplifier produces a constant output signal level for all input signal levels above a maximum input level.

87. The amplifier of claim 86 wherein the maximum input level is in the range 60-90 dB.

88. The amplifier of claim 87 wherein the maximum input level is substantially 70 dB.

89. The amplifier of claim 74 wherein the gain control means controls the amplifier to have a substantially zero gain for input signals below the current estimated noise floor value, such that substantially no output signal is produced when input signals at such levels are received by the amplifier.

90. The amplifier of claim 74 wherein the gain control means controls the amplifier to have a substantially constant gain for input signals below the current estimated noise floor value.

91. The amplifier of claim 74, wherein the amplifier is for providing adaptive operation of a hearing aid.

92. The amplifier of claim 74, wherein the amplifier is for providing adaptive operation of a cochlear implant.

93. The amplifier of claim 74, wherein the amplifier provides linear gain of input signals which are greater in amplitude than the current estimated noise floor value, and are lesser in amplitude than an input signal level at which the amplifier enters infinite compression.

94. The amplifier of claim 74 wherein a slope of the amplifier response in the dynamic range of the amplifier can be adjusted in response to a change in the current estimated noise floor value.

95. The amplifier of claim 94 wherein the slope of the amplifier response is decreased in response to a decrease in the monitored level of background noise.

96. The amplifier of claim 94 wherein, at a perceived moderate level of background noise, the gain of the amplifier is set to a ratio of substantially 1:1 across the dynamic range.

97. The amplifier of claim 96 wherein, when the level of background noise is less than the perceived moderate level, the gain is set to a ratio of substantially 2:1 across the dynamic range.

98. The amplifier of claim 74 wherein an input signal level at which the amplifier enters infinite compression is the same irrespective of the slope of the gain of the amplifying means.

99. The amplifier of claim 74 wherein a slope of the amplifier response in the dynamic range is non-linear.

100. The amplifier of claim 99 wherein the non-linearity of the slope of the amplifier response in the dynamic range varies in response to changes in the current estimated noise floor value.

101. The amplifier of claim 99 or claim 100 wherein, with increasing input signal level, the slope of the amplifier response in the dynamic range is linear at a first ratio to a breakpoint and then linear at a second ratio different to the first ratio, until infinite compression.

102. The amplifier of claim 101 wherein a plurality of breakpoints occur across the dynamic range of the amplifier.

103. The amplifier of claim 101 wherein the slope of the amplifier response is greater for smaller input signal levels, and is reduced for input signal levels above the breakpoint or first breakpoint, such that input signals received at levels above the breakpoint will be partially compressed, relative to input signals at a level below the breakpoint.

104. The amplifier of claim 101 wherein a position of the breakpoint within the dynamic range varies in response to changes in the current estimated noise floor value.

105. The amplifier of claim 101 wherein the first ratio is substantially 1:1 and the second ratio is substantially 2:1.

106. The amplifier of claim 74 wherein the amplifier may be controlled to produce an output signal greater than a maximum comfort level of a user.

107. The amplifier of claim 74 wherein the current estimated noise floor value is determined by monitoring a lowest signal level observed in the input signal within a preceding period of time.

108. The amplifier of claim 107 wherein the period of time is of the order of seconds, to allow for natural breaks in conversation.

109. The amplifier of claim 107 or claim 108 wherein, if an observed lowest signal level in the preceding period of time is lower than the current estimated noise floor value, the current estimated noise floor value is changed to the new lower level.

110. The amplifier of claim 107 wherein, if an observed lowest signal level in the preceding period of time is greater than the current estimated noise floor value, the current noise floor estimate is increased fractionally towards the observed lowest signal level.

111. The amplifier of claim 74 wherein the gain control means is implemented using software executed by a microcontroller.

112. A speech processing means for an auditory prosthesis, the speech processing means comprising:

an amplifying means which is operable to receive an input signal provided by a microphone of the auditory prosthesis, and which is operable to produce an output signal; and a gain control means operable to control the gain of the amplifier in response to a current estimated noise floor value such that the amplifier will only produce an output signal which is greater than or substantially equal to a hearing threshold value when the input signal of the amplifier is greater than or substantially equal to the current estimated noise floor value, and wherein the gain control means is operable to alter the dynamic range of the amplifier in response to a change in the current estimated noise floor value.

113. The speech processing means of claim 112 wherein the current estimated noise floor value is derived from the input signal.

114. The speech processing means of claim 112 or claim 113 wherein the current estimated noise floor value is substantially continuously updated.

115. The speech processing means of claim 112 or claim 113 wherein the current estimated noise floor value is periodically updated.

116. The speech processing means of claim 113 wherein the current estimated noise floor value is derived from the input signal by monitoring an envelope of the input signal and determining the current estimated noise floor value based on detected minima of that envelope.

117. The speech processing means of claim 112 wherein the amplifier gain varies for differing input signal levels.

118. The speech processing means of claim 117 wherein alteration of the amplifier response in the dynamic range responsive to a varying noise floor level is implemented to adapt to an individual user's requirements.

119. The speech processing means of claim 112 wherein a dynamic range of the amplifier is increased in response to a decrease in the current estimated noise floor value.

120. The speech processing means of claim 112 wherein a dynamic range of the amplifier is decreased in response to an increase in the current estimated noise floor value.

121. The speech processing means of claim 112 wherein the amplifier response is continuous, monotonic and increasing for all output signal levels between a hearing threshold value of a user and a maximum comfort value of the user.

122. The speech processing means of claim 112 wherein the amplifier produces an output signal substantially equal in magnitude to the hearing threshold value of a user when the input signal is substantially equal to the current estimated noise floor value.

123. The speech processing means of claim 112 wherein the gain control means ensures that the amplifier does not produce any output signals which exceed a maximum comfort level of a user.

124. The speech processing means of claim 123 wherein the amplifier produces a constant output signal level for all input signal levels above a maximum input level.

125. The speech processing means of claim 124 wherein the maximum input level is in the range 60-90 dB.

126. The speech processing means of claim 125 wherein the maximum input level is substantially 70 dB.

127. The speech processing means of claim 112 wherein the gain control means controls the amplifier to have a substantially zero gain for input signals below the current estimated noise floor value, such that substantially no output signal is produced when input signals at such levels are received by the amplifier.

128. The speech processing means of claim 112 wherein the gain control means controls the amplifier to have a substantially constant gain for input signals below the current estimated noise floor value.

129. The speech processing means of claim 112, wherein the speech processing means is for providing adaptive operation of a hearing aid.

130. The speech processing means of claim 112, wherein the speech processing means is for providing adaptive operation of a cochlear implant.

131. The speech processing means of claim 112, wherein the amplifier provides linear gain of input signals which are greater in amplitude than the current estimated noise floor value, and are lesser in amplitude than an input signal level at which the amplifier enters infinite compression.

132. The speech processing means of claim 112 wherein a slope of the amplifier response in the dynamic range of the amplifier can be adjusted in response to a change in the current estimated noise floor value.

133. The speech processing means of claim 132 wherein the slope of the amplifier response is decreased in response to a decrease in the monitored level of background noise.

134. The speech processing means of claim 132 wherein, at a perceived moderate level of background noise, the gain of the amplifier is set to a ratio of substantially 1:1 across the dynamic range.

135. The speech processing means of claim 134 wherein, when the level of background noise is less than the perceived moderate level, the gain is set to a ratio of substantially 2:1 across the dynamic range.

136. The speech processing means of claim 112 wherein an input signal level at which the amplifier enters infinite compression is the same irrespective of the slope of the gain of the amplifying means.

137. The speech processing means of claim 112 wherein a slope of the amplifier response in the dynamic range is non-linear.

138. The speech processing means of claim 137 wherein the non-linearity of the slope of the amplifier response in the dynamic range varies in response to changes in the current estimated noise floor value.

139. The speech processing means of claim 137 or claim 138 wherein, with increasing input signal level, the slope of the amplifier response in the dynamic range is linear at a first ratio to a breakpoint and then linear at a second ratio different to the first ratio, until infinite compression.

140. The speech processing means of claim 139 wherein a plurality of breakpoints occur across the dynamic range of the amplifier.

141. The speech processing means of claim 139 wherein the slope of the amplifier response is greater for smaller input signal levels, and is reduced for input signal levels above the breakpoint or first breakpoint, such that input signals received at levels above the breakpoint will be partially compressed, relative to input signals at a level below the breakpoint.

142. The speech processing means of claim 139 wherein a position of the breakpoint within the dynamic range varies in response to changes in the current estimated noise floor value.

143. The speech processing means of claim 139 wherein the first ratio is substantially 1:1 and the second ratio is substantially 2:1.

144. The speech processing means of claim 112 wherein the amplifier may be controlled to produce an output signal greater than a maximum comfort level of a user.

145. The speech processing means of claim 112 wherein the current estimated noise floor value is determined by monitoring a lowest signal level observed in the input signal within a preceding period of time.

146. The speech processing means of claim 145 wherein the period of time is of the order of seconds, to allow for natural breaks in conversation.

147. The speech processing means of claim 145 or claim 146 wherein, if an observed lowest signal level in the preceding period of time is lower than the current estimated noise floor value, the current estimated noise floor value is changed to the new lower level.

148. The speech processing means of claim 145 wherein, if an observed lowest signal level in the preceding period of time is greater than the current estimated noise floor value, the current noise floor estimate is increased fractionally towards the observed lowest signal level.

149. The speech processing means of claim 112 wherein the gain control means is implemented using software executed by a microcontroller.

* * * * *